United States Patent
Carnahan et al.

(10) Patent No.: US 7,033,281 B2
(45) Date of Patent: Apr. 25, 2006

(54) AUGMENTED KINEMATIC FEEDBACK DEVICE AND METHOD

(76) Inventors: James V. Carnahan, 1015 W. Charles St., Champaign, IL (US) 61821; David M. Blackshear, 403 McCrary Rd., Molena, GA (US) 30258

(*) Notice: Subject to any disclaimer, the term of this patent is extended or adjusted under 35 U.S.C. 154(b) by 234 days.

(21) Appl. No.: 10/105,051

(22) Filed: Mar. 22, 2002

(65) Prior Publication Data
US 2003/0181832 A1 Sep. 25, 2003

(51) Int. Cl.
A63B 69/00 (2006.01)
A63B 69/36 (2006.01)

(52) U.S. Cl. .................. 473/221; 473/199; 434/247

(58) Field of Classification Search ............. 473/131, 473/201–209, 212–216, 266, 274–277, 408, 473/219–224, 226; 434/247–252; 702/153; 600/547
See application file for complete search history.

(56) References Cited

U.S. PATENT DOCUMENTS

| | | |
|---|---|---|
| 3,820,794 A | 6/1974 | Inoue |
| 3,985,364 A | 10/1976 | Brady |
| 4,175,552 A | 11/1979 | Johnson |
| 4,451,044 A | 5/1984 | Elliott, Jr. |
| 4,660,829 A | 4/1987 | Whiteneir |
| 4,690,142 A | 9/1987 | Ross et al. |
| 4,724,831 A | 2/1988 | Huntjens |
| 4,895,372 A | 1/1990 | Muller |
| 5,108,103 A | 4/1992 | Rilling |
| 5,116,057 A | 5/1992 | Mangiaracina |
| 5,203,568 A | 4/1993 | Vasquez |
| 5,221,088 A | 6/1993 | McTeigue et al. |
| 5,316,017 A | 5/1994 | Edwards et al. |
| 5,368,042 A | 11/1994 | O'Neal et al. |
| 5,372,365 A | 12/1994 | McTeigue et al. |
| 5,375,843 A | 12/1994 | Johnston |
| 5,443,267 A | 8/1995 | Thorson |
| 5,445,385 A | 8/1995 | Brooks |
| 5,478,080 A | 12/1995 | Johnston |
| 5,487,546 A | 1/1996 | Yasuda |
| 5,490,672 A | 2/1996 | Johnston |
| 5,509,809 A | 4/1996 | Clay |
| 5,586,943 A | 12/1996 | Clay |
| 5,588,919 A | 12/1996 | Nakamura |
| 5,655,223 A | 8/1997 | Cozza |
| 5,665,008 A | 9/1997 | Chaney |
| 5,667,447 A | 9/1997 | Perham et al. |
| 5,704,846 A | 1/1998 | Johnson |
| 5,733,201 A | 3/1998 | Caldwell et al. |
| 5,771,492 A | 6/1998 | Cozza |
| 5,823,886 A | 10/1998 | Murray |
| 5,823,980 A | 10/1998 | Kopfer |
| 5,836,829 A | 11/1998 | Van Cotte et al. |
| 5,895,326 A | 4/1999 | Cozza et al. |
| 5,930,741 A | 7/1999 | Kramer |
| 6,487,906 B1 * | 12/2002 | Hock ................. 73/379.01 |

* cited by examiner

Primary Examiner—Mark Sager
(74) Attorney, Agent, or Firm—Fitch, Even, Tabin & Flannery

(57) ABSTRACT

The biomechanical angle of a body joint 11 of a trainee during a given physical activity is continuously monitored and a corresponding audible tracking signal (31, 32, 33, 43, 42, 44) is provided, in real time, to the trainee. This audible tracking signal augments kinematic feedback to the trainee regarding the physical activity and thereby facilitates ease or rapidity of training. In various embodiments, multiple body joints can be monitored, sensitivity of the tracking signal with respect to biomechanical angle excursions can be modified, tracking signals can be recorded for later playback, and a metronome beat can be provided in conjunction with the tracking signal.

22 Claims, 3 Drawing Sheets

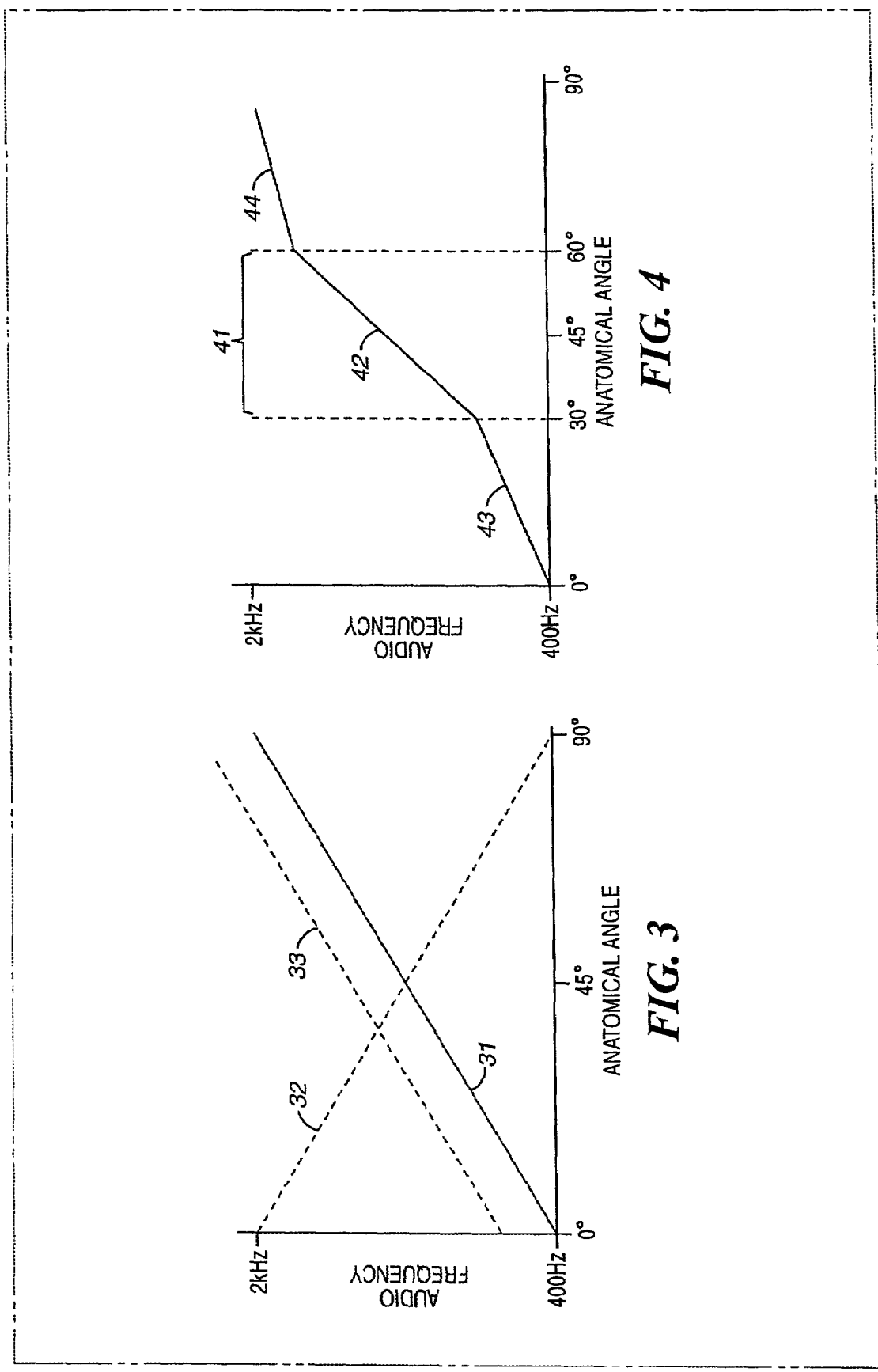

AUGMENTED KINEMATIC FEEDBACK DEVICE AND METHOD

TECHNICAL FIELD

This invention relates generally to physical training and more particularly to physical training as includes at least one body joint.

BACKGROUND

Many physical activities including various sports and therapeutic exercises involve short duration non-reflexive motor programs (often colloquially but incorrectly referred to as "muscle memory"). The specific activity or exercise will typically involve one or more body joints that each constitute a biomechanical angle. Properly executing the activity or exercise will often involve changing that biomechanical angle over time by specific degrees in coordination with other specific actions. Unfortunately the individual exercising the activity will often not be able to directly observe the biomechanical angle in real time, and must rely instead upon their native kinematic feedback (proprioception), comments and instructions from observers, non-real time feedback (as gained, for example, by later watching a video of the activity) and so forth to gain some understanding of this aspect of developing the desired motor program.

Various prior art approaches exist to attempt to supplement and aid the training process. In general, these approaches all suffer from one or more of the following: significant expense, considerable necessary up-front training with respect to the supplemental approach, non-real time feedback, non-intuitive feedback, significant complexity, and/or additional participants are required to facilitate the monitoring and/or evaluate the results. Further, these prior art approaches tend to work by presenting a model (often represented by one or more performance thresholds) against which the individual must seek to conform their own performance. In some instances, or for some individuals, such a model can be effective. But for many other individuals this approach will be inappropriate, confusing, frustrating, and/or counterproductive.

For example, theories abound as to a golfer's proper body positioning and movement during a golf swing. The appropriate time for cocking of the wrists during the backswing, or for bending of the left elbow (for a right-handed golfer), if at all, generates much debate. Further, much can depend on the type of shot to be executed, and the club selected for the shot. Perhaps most importantly, however, the variable that the prior art fails to adequately address is the uniqueness of each golfer's swing in that each individual golfer will likely have different body motions for their ideal golf swing based on their physical abilities and characteristics. For instance, a device that signals a golfer that their swing is deviating from a preset limit with respect to bending or flexing of their elbow or wrist is of little use to a golfer who cannot execute the required body positioning such as due to an injury or other physical limitation.

Accordingly, there is a need for a motion training apparatus or device that better augments a trainee's internal kinematic feedback for motion learning purposes. More particularly, a training device that is not limited to common ideal motion learning for a group of trainees, and is otherwise more universal in its approach to motion learning would be desirable.

BRIEF DESCRIPTION OF THE DRAWINGS

The above needs are at least partially met through provision of the augmented kinematic feedback device and method described in the following detailed description, particularly when studied in conjunction with the drawings, wherein:

FIG. 3 comprises a graph depicting various embodiments of audio frequency augmented kinematic feedback versus biomechanical angle;

FIG. 4 comprises a graph depicting another embodiment of audio frequency augmented kinematic feedback versus biomechanical angle;

Figure 2:
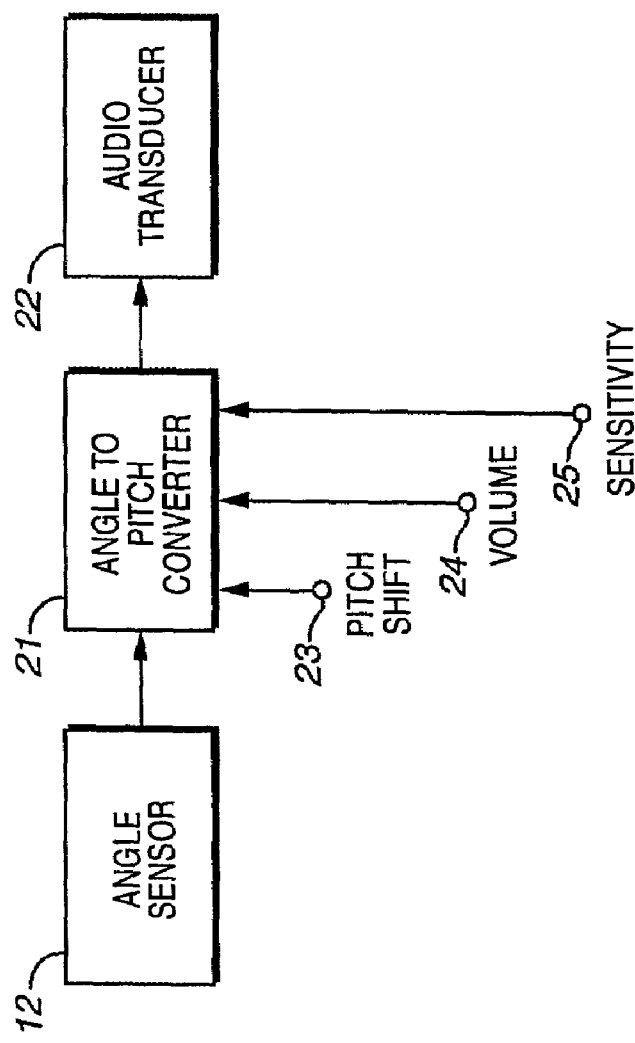
FIG. 2 comprises a block diagram of one embodiment configured in accordance with the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention.

DETAILED DESCRIPTION OF THE PREFERRED EMBODIMENTS

In accordance with the present invention, a training apparatus and method are provided that augment the internal kinematic feedback system of a trainee relating to their body movements via an audible tonal progression that tracks the movement to be trained. Accordingly, the training apparatus and method herein reduce a specific movement of the body, e.g. an arm, knee, or wrist bend, to a distinct, easily discernible and recognizable pattern of tones provided in real-time to the trainee. In this manner, the trainee is able to supplement and enhance or augment their proprioceptive feedback from their muscle/nervous system with a continuum of tones, i.e. in essence a tune, over the range of movement that is easily identifiable by use of the present training apparatus and method.

While golfing comprises an appropriate application of the training device herein and will be used as a basis for examples and explanation, the invention is not so limited and can be used to train body movements generally for other sporting activities like fishing (casting), bowling, tennis, hockey, or soccer to name a few. The trainee's movement when golfing either produces the desired result, e.g. a good golf shot, or an undesired result, e.g. any of a series of poor golf shots. For each shot generated by distinct movements, there will be corresponding distinct tunes or tonal signatures which the trainee can more easily group into those that produced a good golf shot and those that occurred when a bad golf shot was taken. In this regard, the present training apparatus enhances the ability of the trainee to identify and focus in on those motions that are desired from a results-based standpoint as opposed to those that are undesirable since the trainee no longer has to place sole reliance on their native kinematic feedback whose input is not so easily recognized for being later drawn upon for motion repetition except perhaps by gifted athletes.

Thus, the present apparatus provides the user with enhanced sensory perception of their body movements so as to allow the desired aural patterns or tonal signatures to be easily recognized and identified in addition to those patterns or signatures that are not desired in terms of obtaining a good result from the body movement to be undertaken. It is believed that the instantaneous enhanced aural or audio feedback of the apparatus herein will significantly enhance and shorten the usual training period that would normally be required for most individuals to learn a motion as it substantially "evens the playing field" so to speak between the athletically inclined and those less so assuming general equivalence between physical characteristics, e.g. strength and flexibility, and the various relevant types of coordination between individuals as it allows one to more heavily rely on their auditory sense during training as opposed to just their intrinsic proprioceptive feedback.

Moreover, the real-time tracking tune of the motion the joint is undergoing allows the trainee to develop, practice, and learn a motion that is ideal for their physiology and anatomy. So, for the golfing example previously mentioned, the apparatus provides continuous audio feedback so that the golfer has instantaneous and variable tonal information as to the orientation of their body parts during the golf swing. Based upon resulting golf flights, certain distinct tonal signatures of ideal golf swings will become apparent to the golfer. The golfer then attempts to generate these ideal tonal signatures, and avoid the undesired tonal signatures, with future swings. In other words, the present training apparatus, as used for a golf training apparatus for instance, allows a golfer to develop a swing that is highly individualized such that, when substantially replicated, their swing is most likely to produce desirable golf shots for that individual.

The training apparatus and method herein are not typically limited by a user's physique and/or physical limitations or handicaps. Instead, these embodiments can be used to optimize those movements that a trainee is able to undertake in their attempts to achieve a desired or optimal result. Threshold levels of movements are preferably not identified to allow instead for the individualized approach taken by the present training apparatus, although such limits could be incorporated for specific users if they so desire. However, the preferred apparatus is not so restricted and thus does not require one to be able to, for instance, keep their elbows straight through the substantial majority of their golf swing, when such performance is not physically possible. In this manner, the approach of the present apparatus represents a significant departure from that taken by prior training devices which generally integrate threshold movement levels into their systems and identify when these levels have been crossed or exceeded and/or the degree of departure therefrom.

Generally speaking, pursuant to these various embodiments, a sensor is positionable on a trainee's body joint and provides an output that corresponds to a substantially current angle of the body joint. The sensor is effective over a predetermined position continuum with respect to the body joint angle. An electronic signal processor couples to the sensor and provides an output comprising a trainee-discernable real-time audible tracking signal, such that the real-time audible tracking signal corresponds to and tracks the angle of the body joint. The real-time audible tracking signal comprises a user-discernable audible signal that is a part of a user-discernable audible signal continuum that corresponds to the position continuum such that various angles of the biomechanical angle have a corresponding substantially unique user-discernable output.

In one embodiment the tracking signal is provided to the trainee through at least one earphone. Optionally, the earphone could be omitted and a larger speaker utilized to emit sound outwardly therefrom and at levels audible to the trainee so that it can be carried, for instance, on the trainee's belt with the signal still being audible. In another embodiment, the tracking signal is provided to the trainee in conjunction with a periodic signal that serves as a metronome signal. In various embodiments, the audible tracking signal can be adjusted with respect to pitch offset and/or with respect to sensitivity over a specific range of biomechanical angles to be monitored.

So configured, these embodiments provide real-time augmented kinematic feedback to the trainee. This audible feedback, in conjunction with the trainee's own native kinematic feedback (proprioception) as discerned while engaged in the activity of choice, can facilitate development of the proper motor program. Importantly, the audible feedback is completely representative of the trainee's biomechanical angle of choice and is not compared or processed in any way with respect to any predetermined model or standard of desired performance. In effect, this feedback does not initially teach the user how to execute the correct motion. Instead, this feedback provides a powerful mechanism for assisting a user to recognize and replicate correct motion for an activity that the user otherwise perceives as having been done correctly, such as gleaned from the knowledge of the result of the action.

Also importantly, these embodiments can be provided in a cost effective form factor. Operation of the training apparatus or device is relatively intuitive and does not require significant pre-training for effective use. Furthermore, the device is readily usable with a wide variety of body joints and with a wide variety of motor programs as associated with sports, physical therapy, and other physical activities.

Figure 1:
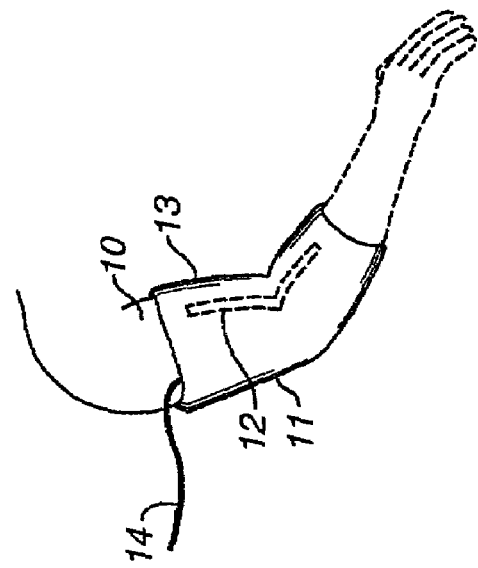
FIG. 1 comprises a perspective view of an exemplary body joint and a biomechanical sensor embodiment configured in accordance with the invention.

Referring now to FIG. 1, a wearable piece of material such as a fabric material formed into a sleeve or cuff 13 or the like is provided for being fit over an exemplary body appendage 10, in this case an arm, having a number of body joints including an elbow 11. The fabric material is flexible and preferably has sufficient resiliency either inherently or as by addition of elastic stretchable material thereto to allow the wearable cuff 13 to stretch such as when the joint 11 is flexed, and then to rebound to its substantially non-flexed state when the joint is straightened. In this manner, the cuff 13 is shape retentive to conform its material relatively tightly about the non-flexed joint in the relaxed state of the cuff material despite repeated flexing of the joint, and can be more readily worn by trainees of various sizes.

A bend sensor 12 as carried by or embedded in the fabric material is disposed axially with respect to the elbow 11 such that the sensor 12 extends across to either side of the elbow 11 when the material is worn thereabout (in this embodiment, the sensor 12 can be positioned either on the inside of the elbow as depicted or on the outside of the elbow). The bend sensor 12 can be comprised, for example, of part number FLX-01 as offered by Images SI Inc. of Staten Island, N.Y. Such a sensor comprises a material (such as conductive ink) having an electrical resistance that varies as the material is bent. The above suggested part exhibits a resistance of about 10K ohms when unbent and a resistance of about 30K to 40K ohms when bent at 90 degrees. With this particular part, additional bending (to about 120 degrees) will increase resistance to about 50K ohms. Other sensors or sensor assemblies could be used if it were necessary to track bending beyond this range. For example, a range of 0 to 180 degrees of bending could be tracked through use of an appropriate sensor mechanism. In general, the sensor selected should be able to track angles of joint movement in excess of or at least corresponding to the maximum range of biomechanical angles that the particular joint can be expected to undergo during the specific activity at hand.

Very little force is required to bend this sensor and its presence will typically not distract the trainee when worn. The sensor 12 can be affixed to respond and track the biomechanical angle in a variety of ways. In a preferred embodiment as depicted, the sensor 12 is embedded in a conforming sleeve 13 that is disposed about the body joint 11 of interest. In this embodiment, a conductor 14 couples between the sensor 12 and the signal processor described below. If desired, of course, a wireless interface (using, for example, Bluetooth short-range communications) could be used to avoid the use of such a conductor.

Referring now to FIG. 2, the angle sensor 12 couples to a signal processor that includes, in this embodiment, an angle to pitch converter 21 and an audio transducer 22. The angle to pitch converter 21 serves to convert the signal from the angle sensor 12 that represents a present angle of the body joint into a corresponding unique audible signal. This audible signal is then rendered audible through the audio transducer 22 (such as one or more earphones as disclosed below). With momentary reference to FIG. 3, it can be seen that for a given range of positions that correspond to a biomechanical angle of the user (in this example, the range extends from 0 degrees to 130 degrees) a corresponding set of user-discernable audible signals 31 will result. In this example, the audible signals 31 range in frequency from about 400 Hz (as corresponds to a biomechanical angle of about 0 degrees) to about 2K Hz (as corresponds to a biomechanical angle of about 90 degrees). In a preferred embodiment the audible tracking signal will tend to increase in frequency as the corresponding angle of the body part increases. If desired, however, the audible tracking signal may tend to decrease in frequency as the corresponding angle of the body part increases (as depicted by the phantom line denoted by reference numeral 32).

The sensor 12 provides essentially real-time and continuous biomechanical angle information to the signal processor, and the latter in turn provides an essentially real-time and continuous audible tracking signal that uniquely corresponds to the then present biomechanical angle. In the preferred example given, as the angle increases, the pitch of the tracking signal increases as well, and as the angle decreases so does the pitch of the tracking signal.

Referring again to FIG. 2, although the signal processing does not compare or contrast the biomechanical angle to any predetermined model or performance threshold, various parameters can be at least slightly modifiable by a user if desired. For example, the overall pitch level for all tracking signals can be shifted by providing a pitch shift control 23. Referring again to FIG. 3, such a pitch shift control 23 can be used to shift the tracking signal upwards (as represented by the phantom line denoted by reference numeral 33) or downwards within some useful range to suit a particular user's preferences and/or abilities. Referring again to FIG. 2, an overall volume control 24 can also be provided to allow the user to control the volume of the tracking signal.

And, if desired, a sensitivity control 25 can be provided to allow a user to adjust sensitivity of changes to the pitch of the tracking signal in response to changes of the biomechanical angle. For example, and referring now to FIG. 4, sensitivity within a given range 41 can be increased such that a given change in the biomechanical angle will yield a greater change in pitch of the corresponding audible tracking signal 42 as compared to other areas of interest where the tracking signal 43 and 44 where the tracking signal will change more gently with respect to changing angles. Such sensitivity alterations can be useful to provide more easily differentiated audible tracking signals for especially important or critical windows of body joint movement. (The example depicted is intended to illustrate this concept only, and it should be understood that sensitivity can be varied in a wide variety of ways including both linear and non-linear resultant envelopes.)

Figure 5:
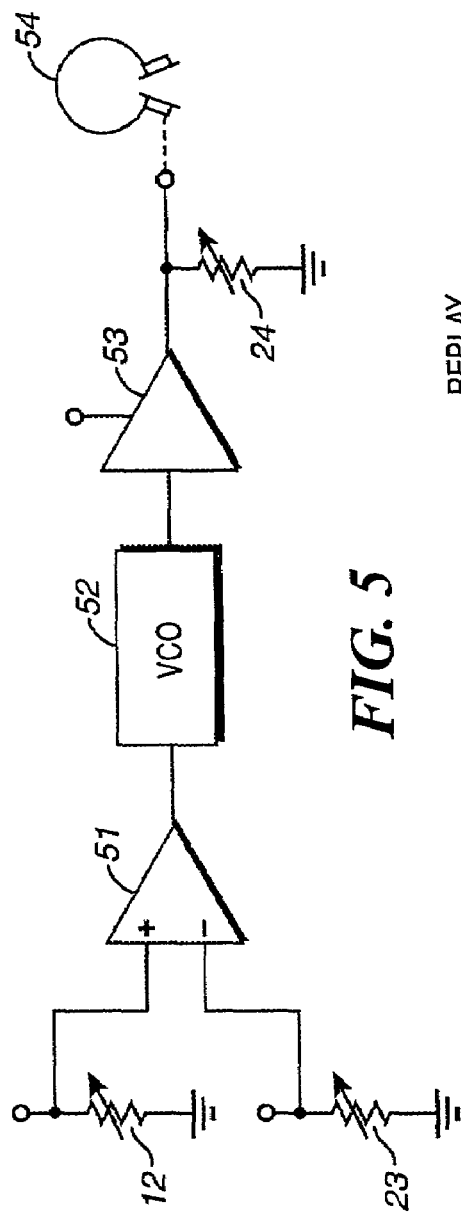
FIG. 5 comprises a schematic representation of an embodiment configured in accordance with the invention.

Referring now to FIG. 5, one simple and relatively inexpensive embodiment will be described. In this embodiment, the biomechanical angle sensor 12 couples to one input an operational amplifier 51, the remaining input of which couples to another variable resistor that serves as a pitch offset adjustment 23 as described above. The output of the operational amplifier 51 feeds a voltage controlled oscillator (VCO) 52 that converts the incoming biomechanical angle signal into a corresponding audible-range signal. This audio signal is then amplified in an audio amplifier 53, adjusted for volume by a master volume control 24, and provided to a pair of earphones 54. This embodiment uses inexpensive components and can be readily packaged in a relatively small housing that is easily worn by the user. The controls are few and relatively intuitive to the user during use. This embodiment again serves to provide real-time audible information that uniquely tracks the monitored body joint to thereby provide augmented kinematic feedback to the user as the physical activity is enacted.

Figure 6:
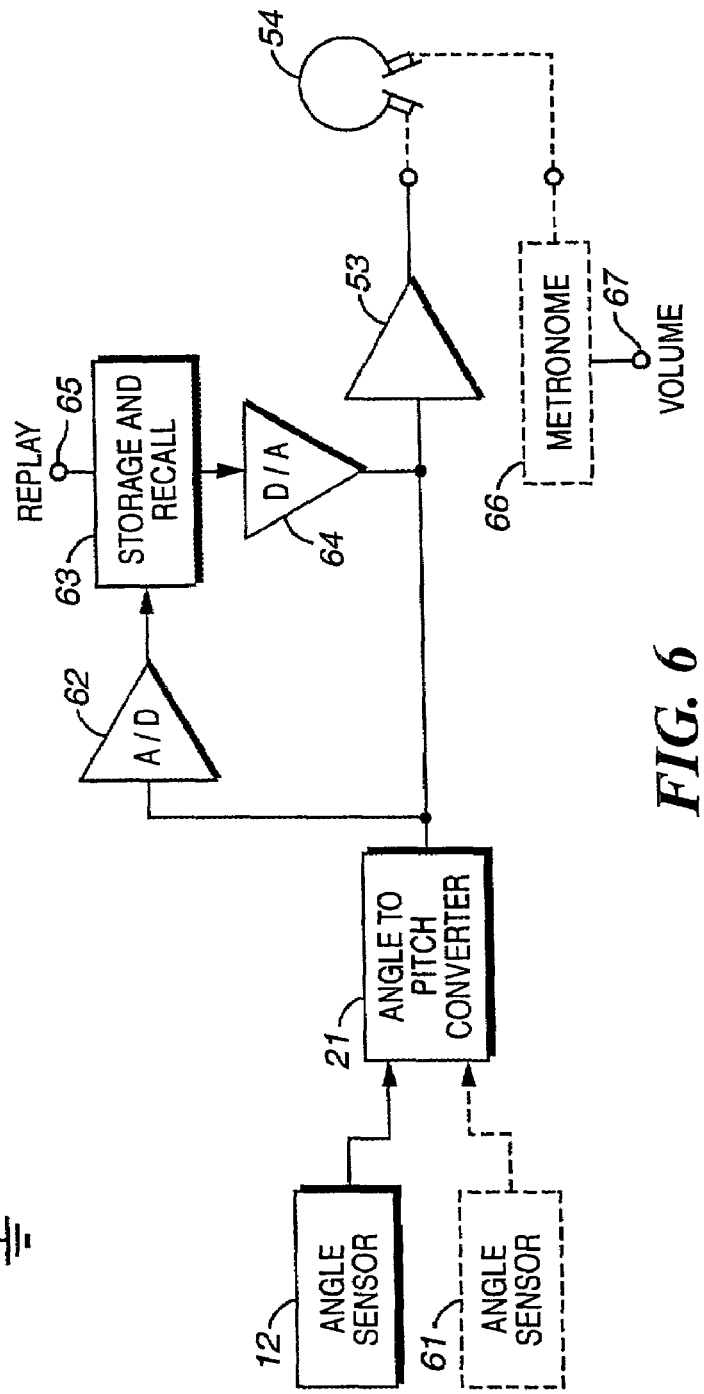
FIG. 6 comprises a block diagram of yet other embodiments configured in accordance with the invention.

Referring now to FIG. 6, other embodiments will now be described. As detailed above, a single angle sensor 12 couples to the angle to pitch converter 21. If desired, and as may be appropriate to specific motor program development activities, additional angle sensors 61 may be used as well. For example, both an elbow and a knee may be simultaneously monitored, or both an elbow and a wrist. When monitoring more than one sensor, the resultant biomechanical angle information can be processed and provided in a variety of ways. For example, audible tracking information for one body joint can be provided to one ear of the user and audible tracking information for a second body joint can be provided to the other ear of the user. Or, the information from all sensors can be combined to yield a single audible tracking signal that represents, in real time, all of the monitored biomechanical angles (such a combination can be a simple summing (weighted or un-weighted) or something more complex as appropriate to a given application). Or, audible tracking information can be provided for a first sensor for a first period of time followed by audible tracking information for a second sensor. This approach can be useful when a first body joint is important to a first portion of a physical activity and a second body joint is important to a second portion of that physical activity. Yet another approach would be to provide only tracking information for a single body joint at a time but to allow the user to switch back and forth between the multiple sensors as desired.

As noted earlier, these embodiments do not use a predetermined model or performance threshold to use in comparison against the real-time performance of the user. If desired, however, a mechanism can be provided to record the audible tracking signal and to allow playback of that recording to the user. For example, the audible tracking signal can be digitized by an analog to digital converter 62 and stored in a storage and recall 63 unit. Such a unit could serve to record multiple events or only a single event as desired. Upon asserting a playback control 65, the stored contents could be passed through a digital to analog converter 64 and passed to the amplifier 53 and earphones 54 to allow the user to hear the replayed tracking signal. Such a capability would allow a user to potentially use the device to more quickly learn a particular desired motor program.

As yet another potential embellishment, a periodic signal comprising a metronome beat can be provided through provision of a metronome unit 66. Such a metronome beat could be provided to one earphone while tracking information is provided to the other ear, or the signals could be mixed together as desired. Also if desired, the metronome unit 66 can be provided with a volume control 67 to allow the level of the metronome beat to be varied to suit a given individual or circumstance. For some individuals, a metronome beat may again assist the trainee to more quickly learn a particular desired motor program.

With any of the embodiments described above, a trainee seeking to gain proficiency with respect to a motor program that corresponds to all or part of a given physical activity (including sports such as golfing and fishing or physical therapy activities) can monitor a biomechanical angle for a body joint that is relevant to the given motor program via an audible signal that tracks, in real time, the biomechanical angle of interest. This audible tracking signal effectively augments kinematic feedback for the user regarding the physical activity and thereby often facilitates the ease or rapidity with which the individual masters the physical activity. This device and method can be used effectively by persons of varying skill levels with respect to the physical activity being learned.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. An apparatus comprising:
    a biomechanical angle sensor positioned to substantially continuously sense a biomechanical angle of a user and having an output that corresponds to the biomechanical angle; and
    an electronic signal device having:
        an input coupled to the output of the biomechanical angle sensor; and
        an output comprising a user-discernable audible signal, which audio signal substantially continuously uniquely corresponds in real-time to a substantially instantaneous output of the biomechanical angle sensor, such that the audible signal as discerned by the user will vary as the user's biomechanical angle varies, wherein the output of the signal device further includes an audible periodic signal.

2. The apparatus of claim 1 wherein the audible periodic signal comprises a metronome beat.

3. The apparatus of claim 1 wherein the output of the signal device comprises a first output for providing the audible signal and a second output for providing the metronome beat.

4. An apparatus for training body movements of a trainee in a highly individualized manner, the apparatus comprising:
    a piece of fabric material configured to be worn at a body joint of the trainee;
    a flex sensor carried in the fabric material so that with the fabric material worn at the body joint, the flex sensor will extend across the joint and will flex as the joint flexes;
    output signals generated by the flex sensor that correspond to different degrees of flexure of the joint; and
    circuitry in electrical communication with the sensor for receiving the output signals therefrom with the circuitry configured to generate audible tones that only vary based on the output signal received but not based on variation of the output signal from a preselected reference value that corresponds to a predetermined model or standard of performance of the trainee so as to generate recognizable tonal signatures each associated with distinct movements of the joint for providing the trainee enhanced sensory perception of their joint movements.

5. The training apparatus for claim 4 wherein the flex sensor is a thin, film sensor having resistive material whose resistance varies as the film sensor is flexed to correspondingly vary the output signals generated therefrom as a function of the degree of flexure of the joint, and the circuitry is calibrated to generate the audible tones as a function of the amount of the variable resistance being created by flexing of the film sensor.

6. The training apparatus of claim 4 wherein the fabric material piece comprises a resilient cuff of material sized to fit about one of the elbow, knee and wrist joints for flexing with the joint and staying in generally tight engagement thereabout with the joint unflexed.

7. The training apparatus of claim 6 wherein the resilient cuff material includes elastic material to allow the cuff material to be worn about joints of different sizes of trainees.

8. The training apparatus of claim 4 wherein the flex sensor generates output signals over a predetermined range of angular bending of the sensor that generally exceeds or corresponds to the maximum movement of bending that can occur at the body joint.

9. The training apparatus of claim 4 wherein the flex sensor generates a predetermined range of output signals and the circuitry generates audible tones having a predetermined range of levels generally corresponding to the range of output signals.

10. The training apparatus of claim 4 wherein the flex sensor comprises a variable resistance sensor.

11. The training apparatus of claim 4 wherein the circuitry generates audible tones that range in frequency from approximately 400 HZ with the flex sensor unbent to approximately 2,000 HZ with the flex sensor bent at a generally ninety degree angle.

12. A method of motion training, the method comprising:
    sensing degrees of flexure of a predetermined body joint that flexes during a predetermined activity of a trainee;
    generating signals that are based on the degrees of joint flexure by the trainee without reference to a preselected reference value that corresponds to a predetermined joint angle of the trainee;
    generating audible tones based on the signals to create a recognizable tonal signature associated with flexing of the joint during the predetermined activity; and
    providing the audible tones in real-time to the trainee as the joint is being flexed to allow the trainee to attempt to replicate tonal signatures the trainee has identified as being associated with desired results from the predetermined activity.

13. The method of claim 12 wherein the predetermined activity comprises a golf swing, and the tonal signatures to be replicated are those associated with a good golf shot.

14. The method of claim 12 including:
providing a resilient piece of material configured to fit about the body joint and carrying a flex sensor therewith; and
positioning the material at the body joint so that the flex sensor spans the joint for sensing the degrees of flexure thereof.

15. The method of claim 12 wherein the body joint has a predetermined angular range of flexure motion, and the audible tones can be generated for substantially the full range of the flexure motion so that continuous audio input is provided to the trainee during the predetermined activity.

16. A method of training an individual with respect to a physical activity that involves at least one body joint, comprising:
while engaged in the physical activity:
continuously monitoring a biomechanical angle that corresponds to the at least one body joint;
providing a substantially contemporaneous audio signal to the individual, which audio signal has at least one user-discernable parameter that changes as a continuous function of changes to the biomechanical angle such that the audio signal tracks the biomechanical angle and thereby augments kinematic proprioceptive feedback to the individual regarding the physical activity without an indication from a change in the signals as to whether a particular body joint angle based on a predetermined model or standard of performance is desirable.

17. A method of training an individual with respect to a physical activity that involves at least one body joint, comprising:
while engaged in the physical activity:
continuously monitoring a biomechanical angle that corresponds to the at least one body joint;
providing a substantially contemporaneous audio signal to the individual, which audio signal has at least one user-discernable parameter that changes as a continuous function of changes to the biomechanical angle such that the audio signal tracks the biomechanical angle and thereby augments kinematic feedback to the individual regarding the physical activity; and
providing a metronome audio signal to the individual contemporaneous with the audio signal.

18. The method of claim 16 and further comprising responding to input from the individual to change the audio signal at a given biomechanical angle with respect to pitch.

19. The method of claim 16 and further comprising responding to input from the individual to adjust sensitivity with respect to how the audio signal changes as a continuous function of changes to the biomechanical angle.

20. The method of claim 16 wherein the physical activity comprises a sport.

21. The method of claim 16 wherein the physical activity comprises physical therapy.

22. The method of claim 16 including initially continuously monitoring of the joint angle without having to initially preset a reference value against which changes in the audio signal parameter are based.

* * * * *